United States Patent
Takami et al.

(10) Patent No.: US 6,898,086 B2
(45) Date of Patent: May 24, 2005

(54) PCB STRUCTURE FOR SCOPE UNIT OF ELECTRONIC ENDOSCOPE

(75) Inventors: Satoshi Takami, Saitama-ken (JP); Yukihiro Ishizuka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/318,108

(22) Filed: Dec. 13, 2002

(65) Prior Publication Data

US 2003/0112608 A1 Jun. 19, 2003

(30) Foreign Application Priority Data

Dec. 14, 2001 (JP) ........................................ 2001-382267

(51) Int. Cl.$^7$ ................................................ H05K 1/14
(52) U.S. Cl. ........................ 361/792; 361/790; 361/719; 439/65; 439/74
(58) Field of Search ................................ 361/792, 719, 361/720, 736, 749, 735, 790, 760, 794, 301.4; 174/250, 50.52; 257/686; 439/74, 65; 348/588, 65, 76

(56) References Cited

U.S. PATENT DOCUMENTS

| | | | | |
|---|---|---|---|---|
| 4,993,405 A | * | 2/1991 | Takamura et al. | 600/110 |
| 5,045,935 A | * | 9/1991 | Kikuchi | 348/71 |
| 5,575,686 A | * | 11/1996 | Noschese | 439/620 |
| 5,754,313 A | * | 5/1998 | Pelchy et al. | 358/473 |

\* cited by examiner

*Primary Examiner*—Kamand Cuneo
*Assistant Examiner*—Hung S. Bui
(74) *Attorney, Agent, or Firm*—Greenblum & Bernstein, P.L.C.

(57) ABSTRACT

A printed circuit board structure for a scope unit of an electronic endoscope system, which is provided with a first printed circuit board formed with a first circuit section, and a second printed circuit board formed with a second circuit section. The first printed circuit board is piled on the second printed circuit board. The second printed circuit board having an area covered with the first printed circuit board and at least one area which is not covered with the first circuit board. The at least one area is used for electrically connecting the second circuit section with an electrical unit other than the second circuit section.

16 Claims, 2 Drawing Sheets

PCB STRUCTURE FOR SCOPE UNIT OF ELECTRONIC ENDOSCOPE

BACKGROUND OF THE INVENTION

Figure 1A:
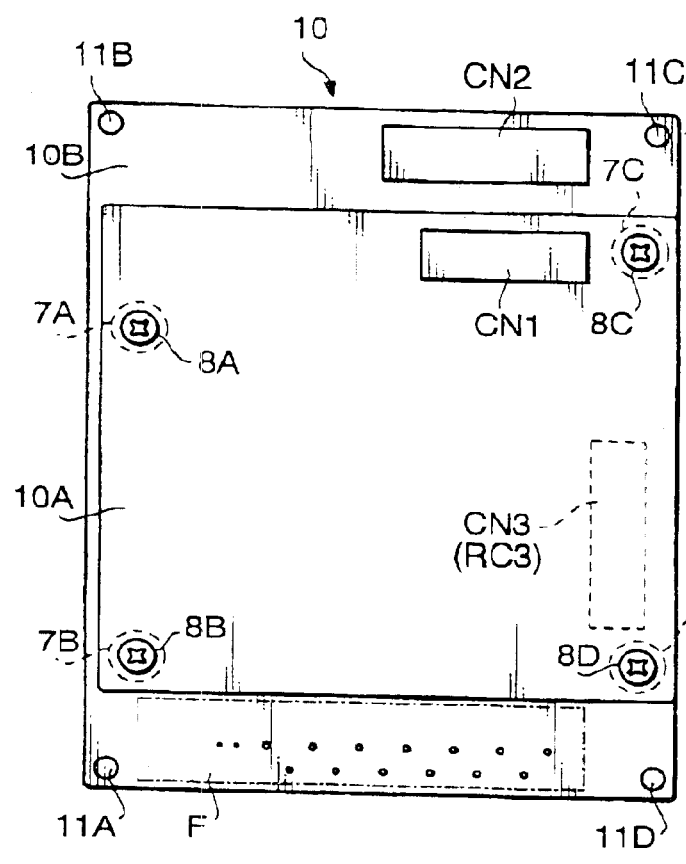

The present invention relates to an electronic endoscope, and more particularly to a PCB (Printed Circuit Board) structure for a scope unit of electronic endoscope.

A medical electronic endoscope is generally provided with a processor having a light source, image processing unit and the like, and an electronic scope (a scope unit) having a portion to be inserted in a human body. The electronic scope has a light guide, which receives the light emitted by the light source from the processor, and illuminates inside the human body, and a CCD (Charge Coupled Device) which captures an image of the illuminated portion.

In such an electronic endoscope, electronic circuits are provided. Typically, an electronic circuit is installed inside a section of the electronic scope in a form of a PCB. In a conventional electronic scope, the PCB is formed of a single substrate having a relatively large area. Generally, such a PCB is provided at a connection section at which the scope unit is connected to the processor. Since the PCB has a relatively large area, the connection section of the endoscope unit becomes large. The large scope unit is troublesome in handling, i.e., in each of operating, carrying and storage, the larger scope is burdensome to the operator.

Conventionally, a structure, in which two PCBs having substantially the same size are piled, has been known. In such a structure, the circuit is divided into two portions, which are formed into the two PCBs respectively.

However, in such a structure, since one circuit pattern is divided into two patterns, if the two PCBs are arranged such that large size electrical elements of the two PCBs are arranged to face outside and the circuit patterns of the two PCBs face each other, it is very troublesome to electrically connect portions of one circuit pattern to portions of the other with wires.

Specifically, after the two PCBs are piled, it is difficult to wire. For example, soldering the wires are difficult with the PCBs piled if the printed patterns face each other. It may be possible to pile the PCBs after the wiring. However, in such a case, the wires are longer than the clearance between the two PCBs, depending on the configuration of the PCBs, and wires and/or soldered portions may easily be broken. Therefore, the piling procedure should be performed with the greatest care. If the PCBs are arranged such that the circuit patterns are located outside the piled PCBs, room for wires connecting the PCBs is required, which obstructs downsizing of the electronic scope.

SUMMARY OF THE INVENTION

The present invention is advantageous in that an improved PCB structure is provided, in which the electrical connection between two patterns respectively provided on piled PCBs can be done relatively easily, and wires connecting the patterns may not be broken easily.

According to an aspect of the invention, there is provided a printed circuit board structure for a scope unit of an electronic endoscope system, which is provided with a first printed circuit board formed with a first circuit, and a second printed circuit board formed with a second circuit. The first printed circuit board is piled on the second printed circuit board with a predetermined clearance therebetween. The second printed circuit board having an area covered with the first printed circuit board and at least one area which is not covered with the first circuit board. The first circuit is electrically connected with the second circuit, and the at least one area is used for electrically connecting the second circuit with an electrical unit other than the second circuit.

According to another aspect of the invention, there is provided an electronic endoscope system having a scope unit, processor and a monitor. The scope unit has a printed circuit board structure, which includes a first printed circuit board formed with a first circuit, and a second printed circuit board formed with a second circuit. The first printed circuit board is piled on the second printed circuit board with a predetermined clearance therebetween. The second printed circuit board has an area covered with the first printed circuit board and at least one area which is not covered with the first circuit board. The first circuit is electrically connected with the second circuit. The at least one area is used for electrically connecting the second circuit with an external electrical unit.

With this configuration, even though the printed circuit boards are piled, the electrical connection can be made easily, and the connected portion (i.e., soldered portion and/or a portion provided with a connector) may not be broken easily.

Optionally, the second circuit may be connected with the electrical unit with wires, which are soldered to the second circuit at the at least one area.

In one case, the electrical unit may include an imaging element provided to the scope unit. A connector is provided at the at least one area, and the second circuit is connected with the electrical unit through the connector.

In this case, the electrical unit may include a monitor of the electronic endoscope system.

Alternatively, the electrical unit includes a processor of the electronic endoscope system.

In a particular case, the first circuit and the second circuit may face each other.

Optionally, with this structure, one of the first and second printed circuit boards is provided with a connector within an area where the first printed circuit board covers the second printed circuit board, and the other of the first and second printed circuit boards is provided with a receptor that receives the connector, the first circuit and the second circuit being electrically connected through the connector and receptor.

Still optionally, the first circuit maybe a digital circuit and the second circuit may be a analog circuit.

Preferably, the second circuit is grounded.

BRIEF DESCRIPTION OF THE ACCOMPANYING DRAWINGS

Figure 1C:
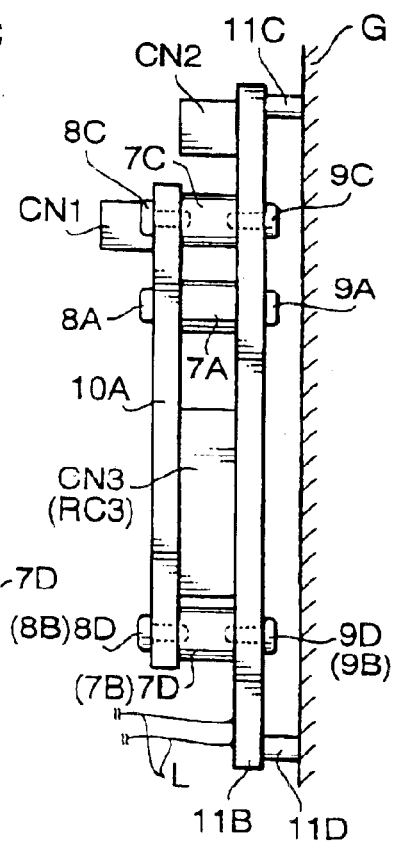
Figure 1B:
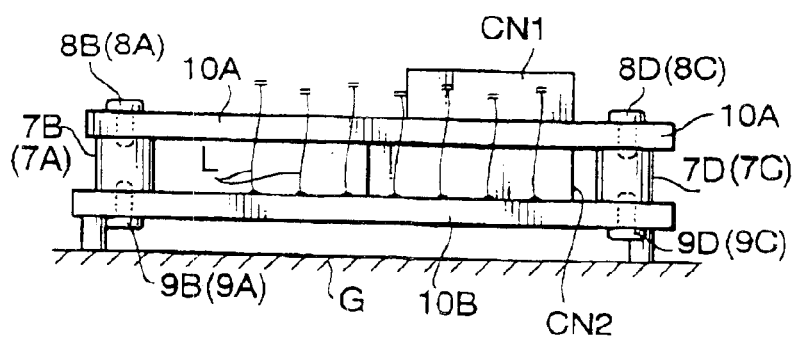
Figure 2:
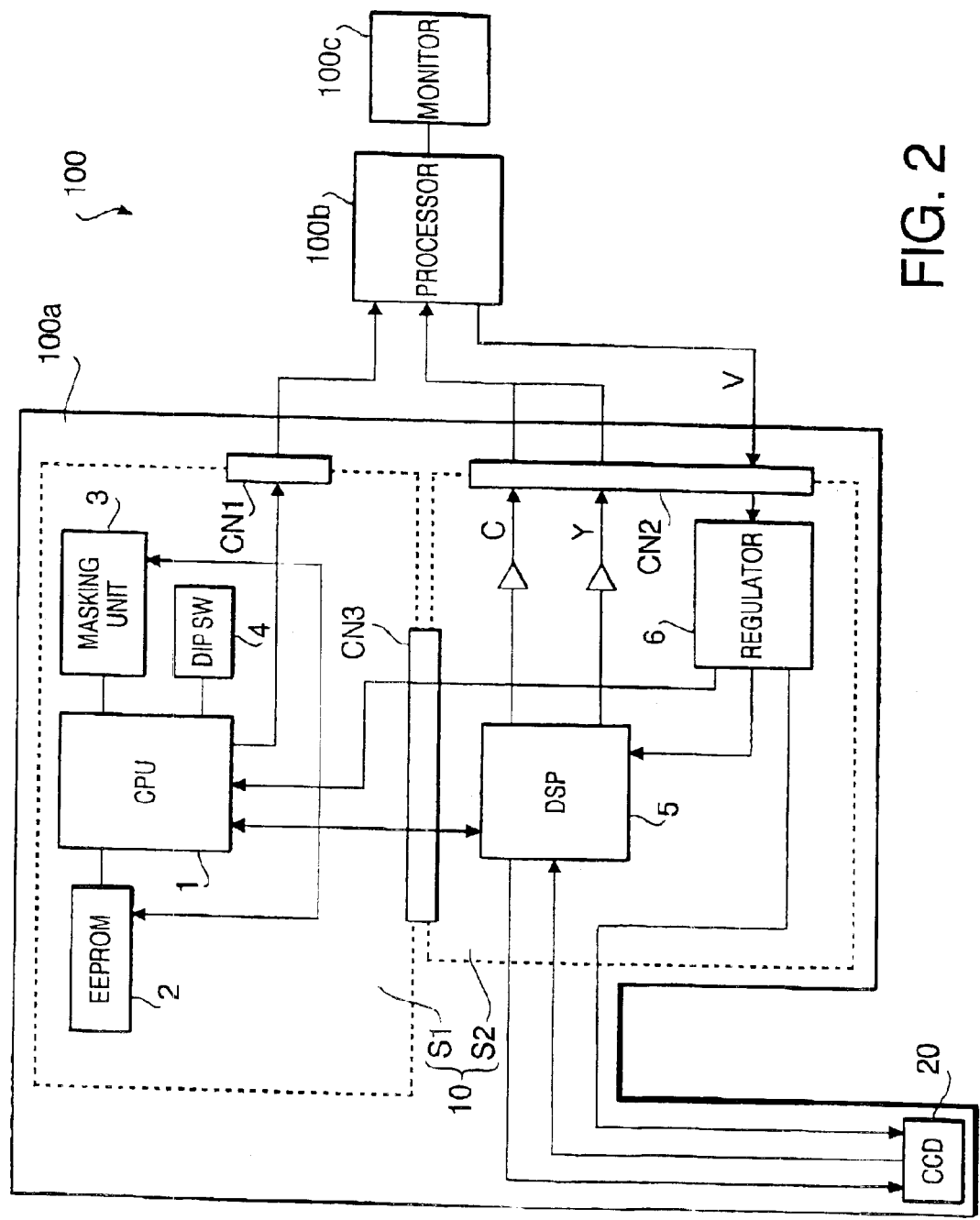

FIGS. 1A–1C are a plan view, a front view and a side view of the PCB structure according to an embodiment of the invention, respectively; and FIG. 2 is a block diagram illustrating an electrical configuration of the electronic endoscope according to the embodiment of the invention.

DETAILED DESCRIPTION OF THE EMBODIMENT

FIGS. 1A–1C are a plan view, a front view and a side view of the PCB structure, respectively. The PCB structure is employed in an electronic endoscope system 100 (hereinafter, occasionally referred to as endoscope system)

according to an embodiment of the invention. FIG. 2 is a block diagram illustrating an electrical configuration of the electronic endoscope system 100.

The endoscope system 100 includes a scope unit 100a, a processor unit 100b and a monitor 100c. A CCD 20 is provided at a tip end (distal end) of the scope unit 100a.

Although not shown in the drawings, the processor unit 100b is provided with a power unit for providing electrical power to the connected scope unit 100a, a light source unit for providing light to the scope unit 100a for illuminating an object to be observed, and an image processing unit that processed an image signal captured by the CCD 20 and transmitted from the scope unit.

The scope unit 100a includes a driving unit 10 which controls an electrical operation of the scope unit 100a. The driving unit 10 is divided into two (i.e., first and second) circuit sections S1 and S2.

The first circuit section S1 mainly controls an entire operation of the scope unit 100a and is formed as a digital circuit. The first circuit section S1 includes a CPU 1, EEPROM 2, a masking unit 3 and a dip switch 4.

Further, the second circuit section S2 mainly processes an image signal output by the CCD 20 and generates an analog video signal. The second circuit section S2 is formed as an analog circuit, which includes a DSP (Digital Signal Processor), a regulator 6 and the like. The regulator 6 functions as a main portion of a power circuit of the scope unit 100a. It should be noted that, regarding the number of elements included in the circuits, the first circuit section S1 includes fewer elements than the second circuit section S2, although indicated in the drawings.

As shown in FIGS. 1A–1C, the driving unit 10 includes two PCBs (printed circuit boards) 10A and 10B having a piled structure.

According to the embodiment, the first and second circuit sections S1 and S2 are formed on the PCBs 10A and 10B, respectively.

The driving unit 10 is provided at a portion, inside the scope unit 100a and close to a part of the scope unit 100a to be connected with the processor unit 100b. Since the driving unit 10 can be downsized as described above, the part of the scope unit 100a to be connected with the processor unit 100b can be downsized. According to the embodiment, the scope unit 100a can be quite operative, and, unnecessary burden will not be provided to a user of the scope unit 100a.

As shown in FIGS. 1A–1C, the first PCB 10A is provided with a connector CN1 for connecting the first circuit section S1 with the processor 100b, and a connector CN3 for connecting the first circuit section S1 with the second circuit section S2.

The second PCB 10B is provided with a connector CN2 for connecting the second circuit section S2 with the processor 100b, and a receptor RC3 to which the connector CN3 is connected. Further, the second PCB 10B is provided with an area F at which the second circuit section S2 and CCD 20 are connected with wires L.

It should be noted that each of the first PCB 10A and second PCB 10B has a rectangular shape, and the first PCB 10A is formed to be smaller at least in a direction parallel to one side of the rectangular shape. Further, the first and second PCBs 10A and 10B are piled such that both end side portions of the second PCB 10B have areas which are not covered with the first PCB 10A. One of the uncovered areas is formed with the connector CN2, and the other of the uncovered areas is defined as the area F.

It should be noted that, according to the embodiment, the first PCB 10A is provided with fewer elements than the second PCB 10B, (i.e., the digital circuit (the first circuit section S1) has fewer elements than the analog circuit (the second circuit section S2) has, and therefore, the first PCB 10A can be made smaller than the second PCB 10B. Although not shown in the drawings, the center of the first PCB 10A and the center of the second PCB 10B substantially coincide with each other.

Since the area F at which wires L are soldered is not covered by the upper PCB (i.e., the first PCB 10A), the soldering operation and the like can be executed relatively easily. Further, since the connector CN2 is exposed, a connector (not shown) for connecting the connector CN2 to the processor 100b can be easily inserted in the connector CN2.

Furthermore, since the first PCB 10A does not exist above the connector CN2 and the area F, the wires L and connectors at these areas may not be bent more than necessary, and/or damaged by the first PCB 10A, and a connection condition can be maintained, which suppresses malfunctions caused by the conventional structure.

In the embodiment, the weirs leading from the CCD 20 are soldered on the second PCB 10B. This configuration may be modified such that the wires L from the CCD 20 are collected to form a connector, and a receptor of receiving the thus formed connector is provided at the area F.

A clearance that prevents short of circuitries between the first and second PCBs 10A and 10B is determined in accordance with the height, with respect to the second PCB 10B, of an element on the second circuit section S2 (i.e., the second PCB 10B) within an area covered with the first PCB 10A.

According to the embodiment, the clearance is determined substantially the same as the height of the connector CN3.

The width of the clearance is defined by the height of spacers 7A through 7D. Each of the spacers 7A, 7B, 7C and 7D has a cylindrical shape formed with two threaded holes at end portions thereof.

By screwing screw 8A and 9A, with the first PCB 10A, the spacer 7A, and the second PCB 10B therebetween, screwing 8B and 9B with the first PCB 10A, the spacer 7B and the second PCB 10B therebetween, screwing 8C and 9C, with the first PCB 10A, the spacer 7C and the second PCB 10B therebetween, screwing 8D and 9D with the first PCB 10A, the spacer 7D and the second PCB 10B therebetween, the first and second PCBs 10A and 10B are integrally secured with the necessary clearance therebetween.

It should be noted that, according to the embodiment, the spacers 7A–7D has a cylindrical shape. However, the shape of the spacers 7A–7D need not be limited to the cylindrical shape, and any other suitable shape can be employed.

The second PCB 10B is secured in a casing G (see FIG. 1C) provided in the scope unit 100a via conductive members 11A–11D which combine the ground pattern of the second circuit section S2 to the flame ground of the casing G. The second circuit section S2 formed on the second PCB 10B may be affected by noises relatively easily since it includes an analog circuit. Therefore, by using the conductive members 11A–11D for supporting the second PCB 10B to ground the second circuit section S2, the noises can be removed by the electromagnetic shielding and a stable operation of the second circuit section S2 is ensured.

Hereinafter, with reference to FIG. 2, an operation of the endoscope system 100 will be described.

The CPU 1 controls the entire operation of the scope unit 100a. The CPU 1 drives the scope unit 100a in accordance with settings transmitted from external devices (not shown) and/or settings of the DIP switch 4. The CPU 1 transmits/receives signals to/from the second circuit section S2 through the connector CN3. Further, the CPU 1 transmits a timing signal to the processor 100b through the connector CN1. The CPU 1 retrieves necessary data for driving the scope unit 100a from the EEPROM 4.

The DSP 5 outputs a timing signal for the CCD 20, receives the image signal from the CCD 20, and generates analog image signals, i.e., color difference signal C and brightness signal Y. The color difference signal C and the brightness signal Y are amplified and transmitted to the processor unit 100b through the connector CN2.

According to the embodiment, the CPU 1 receives masking data transmitted from the masking unit 3, and transmits a mask processing signal to the DSP 5. Thus, when the color difference signal C and the brightness signal Y are generated, the masking process is simultaneously performed. By the masking process, a peripheral portion of an image displayed on the monitor 100c is masked and displayed as a black area, which improves appearance of the displayed image.

The electrical power is supplied from the processor unit 100b to the regulator 6 through the connector CN2. The regulator 6 converts the supplied voltage into optimum voltages for electrical units inside the scope unit 100a, respectively, and applies the converted voltages to respective electrical units. As described above, the power source unit including the regulator 6 is provided on the second PCB 10B bearing the second circuit section S2. Operation of the analog circuit easily becomes unstable when noises are applied and/or predetermined voltage is not applied. Thus, according to the embodiment, the power source unit is located within the analog circuit (i.e., the second circuit section S2), so that the voltages are applied to respective units of the second circuit S2 before being affected by noises.

It should be noted that the voltages are supplied to units in the first circuit section S1, e.g., the CPU 1, through the second PCB 10B and the connector CN3. Since the units of the digital circuit (i.e., the first circuit section S1) remain stable if fluctuation of voltages and/or noises are generated, even if lines through which voltages are applied to the second circuit section S2 are relatively long, it is expected that the scope unit 100a operates stably.

By dividing an entire circuitry into the digital circuit and the analog circuit, and providing the same on different PCBs 10A and 10B, it becomes easier to judge which PCB malfunctions when the entire circuitry malfunctions. Further, in such a case, only the PCB having the defects may be replaced, thereby lowering maintenance costs.

In particular, since elements of a digital circuit improves in quality quickly, the PCB bearing the digital circuit may be replaced with another PCB of a higher version. On the other hand, the analog circuit may not improved as quickly. For example, frequency settings of the DSP 5 is adjusted to an individual difference of the CCD 20. If the analog circuit is provided on the same PCB bearing as the digital circuit, the analog circuit should be replaced when the digital circuit is replaced. In such a case, the adjustment of the elements of the analog circuit as exemplified above should be performed, which requires a troublesome process.

According to the above-described embodiment, since the digital circuit and the analog circuit are provided on different PCBs, the above problem can be avoided.

It should be noted that the foregoing is an exemplary embodiment, and the present invention is not limited to the above-described configuration. Rather, the structure may be modified in various ways without departing from the scope of the invention.

For example, the size and shape of the PCBs are not limited to the PCBs described above. In the above-described embodiment, in view of stability, the two PCBs 10A and 10B are arranged such that the center positions thereof substantially coincide with each other when two PCBs are piled. However, this can be modified and the two PCBs can be arranged so that a sufficient area of uncovered portion(s) is formed on the second PCB 10B. In a particular case, both PCBs may be the same size and shifted to provide an area for the connector(s) and soldering portion(s).

In the embodiment, the two PCBs are formed with digital and analog circuits, respectively. However, the invention is not limited to such a configuration. For example, elements which may be replaced frequently may be provided on one PCB and elements which may not be replaced so frequently may be provided on the other PCB.

In the above-described embodiment, the DSP 5 is employed to downsize the PCB. However, the invention need not be limited to one employing the DSP, and any equivalent, which may have a plurality of elements, may replace the DSP 5.

In the above-described embodiment, the light source is provided in the processor unit 100b. However, the light source need not always be provided to the processor 100b, and another configuration, for example, an LED provided in the vicinity of the CCD 20 may be used.

The present disclosure relates to the subject matter contained in Japanese Patent Application No. 2001-382267, filed on Dec. 14, 2001, which is expressly incorporated herein by reference in its entirety.

What is claimed is:

1. A printed circuit board structure for a scope unit of an electronic endoscope system, said structure comprising:
   a first printed circuit board provided with a first circuit section;
   a second printed circuit board provided with a second circuit section, said second printed circuit board including a surface facing the first printed circuit board, the surface having an area that is covered with said first printed circuit board and having at least one area that is not covered with said first printed circuit board; and
   wires which are soldered to said second circuit section at said at least one area such that said wires extend in a direction from said second printed circuit board to said first printed circuit board,
   wherein said first printed circuit board is positioned on said second printed circuit board, and
   wherein said at least one area is used for electrically connecting said second circuit section to an electrical unit other than said second circuit section with said wires.

2. The structure according to claim 1, wherein the electrical unit includes an imaging element provided to said scope unit.

3. The structure according to claim 1, wherein a connector is provided at said at least one area, and wherein said second circuit section is connected to the electrical unit through said connector.

4. The structure according to claim 3, wherein the electrical unit includes a processor of the electronic endoscope system.

5. The structure according to claim 1, wherein circuit patterns of said first circuit section and said second circuit section face each other with a predetermined clearance therebetween.

6. The structure according to claim 5, wherein one of said first and second printed circuit boards is provided with a connector within an area where said first printed circuit board covers said second printed circuit board, and the other of said first and second printed circuit boards is provided with a receptor that receives said connector, said first circuit section and said second circuit section being electrically connected through said connector and receptor.

7. The structure according to claim 1, wherein said first circuit section is a digital circuit and said second circuit section is a analog circuit.

8. The structure according to claim 7, wherein said second circuit section is electromagnetically shielded.

9. An electronic endoscope system having a scope unit, a processor and a monitor, said scope unit having a printed circuit board structure, said structure comprising:

a first printed circuit board provided with a first circuit section;

a second printed circuit board provided with a second circuit section, said second printed circuit board including a surface facing the first printed circuit board, the second printed circuit board having an area that is covered with said first printed circuit board and having at least one area that is not covered with said first printed circuit board; and wires which are soldered to said second circuit section at said at least one area such that said wires extend in a direction from said second printed circuit board to said first printed circuit board, wherein said first printed circuit board is positioned on said second printed circuit board, and wherein said at least one area is used for electrically connecting said second circuit section to an electrical unit of the electronic endoscope system other than said second circuit section with said wires.

10. The system according to claim 9, wherein the electrical unit includes an imaging element provided to said scope unit.

11. The system according to claim 9, wherein a connector is provided at said at least one area, and wherein said second circuit section is connected to the electrical unit through said connector.

12. The system according to claim 11, wherein the electrical unit includes a processor of the electronic endoscope system.

13. The system according to claim 9, wherein circuit patterns of said first circuit section and said second circuit section face each other with a predetermined clearance therebetween.

14. The system according to claim 13, wherein one of said first and second printed circuit boards is provided with a connector within an area where said first printed circuit board covers said second printed circuit board, and the other of said first and second printed circuit boards is provided with a receptor that receives said connector, said first circuit section and said second circuit section being electrically connected through said connector and receptor.

15. The system according to claim 9, wherein said first circuit section is a digital circuit and said second circuit section is an analog circuit.

16. The system according to claim 15, wherein said second circuit section is electromagnetically shielded.

* * * * *